United States Patent [19]

Junino et al.

[11] Patent Number: 5,015,769
[45] Date of Patent: May 14, 1991

[54] 3-AMINO-4-NITROPHENOLS, THE PROCESS FOR PREPARATION THEREOF AND THEIR USE IN DYEING KERATINOUS FIBERS, AND NEW INTERMEDIATE 4,5-DINITROPHENOLS

[75] Inventors: Alex Junino, Livry-Gargan; Gerard Lang, Saint-Gratien; Alain Genet, Aulnay-sous-Bois, all of France

[73] Assignee: L'Oreal, Paris, France

[21] Appl. No.: 540,263

[22] Filed: Jun. 19, 1990

Related U.S. Application Data

[60] Continuation of Ser. No. 140,797, Jan. 5, 1988, abandoned, which is a Division of Ser. No 850,695, Apr. 11, 1986, Pat. No. 4,740,622.

[30] Foreign Application Priority Data

Apr. 16, 1985 [LU] Luxembourg .................... 85852

[51] Int. Cl.$^5$ ............................................ C07C 213/00
[52] U.S. Cl. .................... 564/399; 564/441; 568/587; 568/652
[58] Field of Search ................ 564/399, 441; 568/587, 568/652

[56] References Cited

U.S. PATENT DOCUMENTS 1,792,716  2/1931  Stockelbach .................... 568/652
4,609,759  9/1986  Carr .................... 564/406

OTHER PUBLICATIONS

Parijs, A. H., *Rec. Trav. Chim.*, vol. 49, pp. 45–56, (1930).

*Primary Examiner*—Richard L. Raymond
*Assistant Examiner*—Scott C. Rand
*Attorney, Agent, or Firm*—Cushman, Darby & Cushman

[57] ABSTRACT

New 3-amino-4-nitrophenols, the process for preparation thereof and their use in dyeing keratinous fibers, and new intermediate 4,5-dinitrophenols.

The present invention relates to a 3-amino-4-nitrophenol of formula:

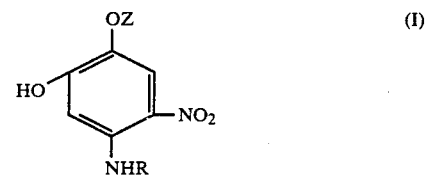

(I)

where Z denotes —$CH_2$—W, W denoting hydrogen, $C_1$-$C_6$ alkyl, $C_1$-$C_6$ hydroxyalkyl, $C_2$-$C_6$ polyhydroxyalkyl, ($C_1$-$C_3$)alkoxy($C_1$-$C_6$)alkyl or ($C_1$-$C_3$)hydroxyalkoxy($C_1$-$C_6$)alkyl and R denotes hydrogen, $C_1$-$C_6$ alkyl, $C_1$-$C_6$ hydroxyalkyl, $C_2$-$C_6$ polyhydroxyalkyl or ($C_1$-$C_3$)alkoxy($C_1$-$C_6$)alkyl, the process for preparation thereof and the intermediate compound of formula:

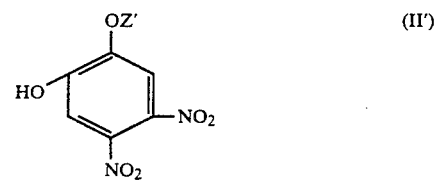

(II')

in which Z' denotes $CH_2$—W, W denoting $C_1$-$C_6$ hydroxyalkyl, $C_2$-$C_6$ polyhydroxyalkyl, ($C_1$-$C_3$)alkoxy-($C_1$-$C_6$)alkyl or ($C_1$-$C_3$)hydroxyalcoxy($C_1$-$C_6$)alkyl.

The dyes (I) are useful in direct dyeing of keratinous fibers, in particular human hair.

7 Claims, No Drawings

3-AMINO-4-NITROPHENOLS, THE PROCESS FOR PREPARATION THEREOF AND THEIR USE IN DYEING KERATINOUS FIBERS, AND NEW INTERMEDIATE 4,5-DINITROPHENOLS

This is a continuation of application Ser. No. 07/140,797, filed Jan. 5, 1988, now abandoned, which is a division of application Ser. No. 06/850,695, filed Apr. 11, 1986, now U.S. Pat. No. 4,740,622.

The present invention relates to new 3-amino-4-nitrophenols, the process for preparation thereof and their use for dyeing keratinous fibres, and especially human hair, and also to the intermediate 4,5-dinitrophenols.

In the field of hair dyeing, it is well-known to use so-called oxidation dyes, which perform very well from the technical standpoint in that they lead to shades which have very good covering power and are tenacious. However, these dyes cause the appearance of the phenomenon of boundaries between dyed ends and half-lengths and undyed roots, due to the regrowth of the hair.

For this reason, increasingly frequent use is being made of direct dyes which, by virtue of the variety of possible substituents, enable a broad spectrum of tones to be covered, ranging from yellow to blue passing through red, without it being necessary to lighten the colour of the hair. Added to the fact that these dyes are less resistant to washing, this leads to the disappearance of the phenomenon of boundaries due to regrowth.

Furthermore, these direct dyes, and more precisely the nitrated benzene dyes, which perform best, are also very well tolerated.

However, direct dyes are not free from disadvantages. They are criticized, inter alia, for being insufficiently resistant to washing and light.

During its investigations, the Applicant discovered that it was possible to obtain hair dyes possessing good stability to light, washing and adverse weather conditions by means of a special family of nitroaminophenols. These special nitroaminophenols are yellow dyes, which are in great demand in direct dyeing for obtaining natural tints.

Furthermore, in addition to their dyeing qualities, these dyes possess the property of being very harmless.

The subject of the present invention is consequently new 3-amino-4-nitrophenols of formula:

[Structure (I): benzene ring with OZ, HO, NO$_2$, NHR substituents]

in which:
- Z denotes a group —CH$_2$—W, W denoting a hydrogen atom or a C$_1$-C$_6$ and preferably C$_1$-C$_4$ alkyl, C$_1$-C$_6$ hydroxyalkyl, C$_2$-C$_6$ polyhydroxyalkyl, (C$_1$-C$_3$)alkoxy(C$_1$-C$_6$)alkyl or (C$_1$-C$_3$)hydroxyalkoxy(C$_1$-C$_6$)-alkyl radical, and
- R denotes a hydrogen atom or a c$_1$-C$_6$ alkyl, C$_1$-C$_6$ hydroxyalkyl, C$_2$-C$_6$ polyhydroxyalkyl or (C$_1$-C$_3$)-alkoxy(C$_1$-C$_6$)alkyl radical.

By way of preferred radicals Z, methyl, ethyl, n-propyl, n-butyl, β-hydroxyethyl, γ-hydroxypropyl, β, γ-dihydroxypropyl, β-methoxyethyl, β-ethoxyethyl and β, γ-hydroxyethoxyethyl radicals may be mentioned.

By way of preferred radicals R, hydrogen and methyl, ethyl, n-propyl, n-butyl, β-hydroxyethyl, γ-hydroxypropyl, β, γ-dihydroxypropyl, β-methoxyethyl and β-ethoxyethyl radicals may be mentioned.

Among the compounds of formula (I), the following preferred compounds may be mentioned:
5-amino-2-methoxy-4-nitrophenol
5-n-butylamino-2-methoxy-4-nitrophenol
5-(γ-hydroxypropyl)amino-2-methoxy-4-nitr
5-methylamino-2-(β-hydroxyethoxy)-4-nitrophenol
5-(β-methoxyethyl)amino-2-[β-(2-hydroxyethoxy)ethoxy]-4-nitrophenol The process for preparing the compounds of formula (I), which constitutes another subject of the invention, can be summarized by the scheme below:

[Reaction scheme: 1,2-dinitro-4,5-methylenedioxybenzene → (II) 4,5-dinitro compound with OZ and HO → (I) 3-amino-4-nitrophenol with OZ, HO, NO$_2$, NHR via Z—OH/(KOH) then RNH$_2$]

Z and R having the meaning given above.

In a first stage, the compounds of formula (II) are prepared by the action of the alcohol ZOH, in the presence of a strong base such as potassium hydroxide, on 1,2-dinitro-4,5-methylenedioxybenzene, the alcohol ZOH, used in excess, serving as a solvent. The reaction temperature generally varies between 20° C. and 200° C., and can be the refluxing temperature of the alcohol ZOH.

In place of the alcohol ZOH and the strong base, the sodium or potassium alcoholate can be used.

The compounds of formula (II) in which Z denotes a methyl or ethyl radical are known, and are prepared by treatment of 4,5-methylenedioxy-1,2-dinitrobenzene either with a solution of sodium methylate in methanol, or with a solution of sodium ethylate in ethanol [PARIJS, Rec. trav. chim. 49, p 33–44 (1930) and SHIGERU KOBAYASHI, Masaru KIHARA and YOSHINOBU YAMAHARA, Chem. Pharm. Bull. p. 3113 26 (1978)].

In a second stage, the compounds of formula (I) are prepared in good yield by selective substitution of the NO$_2$ group in the para position to the OZ group by an —NHR group, using ammonia or an amine RNH$_2$. This substitution is generally carried out in the presence of polar solvents such as water, C$_1$-C$_4$ lower alcohols or amides. However, the presence of the solvent is not necessary.

In the case where ammonia or methylamine is used, the reaction is performed under pressure (5 to 6 kg/cm$^2$) in an autoclave.

The reaction temperature is the refluxing temperature of the reaction medium; the temperature of 100° C. is generally sufficient.

Another subject of the invention consists of the intermediate compounds of formula (II'):

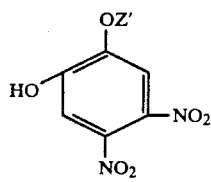

(II')

in which Z' denotes a group CH$_2$—W, W denoting a C$_1$–C$_6$ hydroxyalkyl, C$_2$–C$_6$ polyhydroxyalkyl, (C$_1$–C$_3$)alkoxy(C$_1$–C$_6$)alkyl or (C$_1$–C$_3$)hydroxyalkoxy(C$_1$–C$_6$)alkyl radical.

Preferred radicals Z' are β-hydroxyethyl, γ-hydroxypropyl, β, γ-dihydroxypropyl, β-methoxyethyl, β-ethoxyethyl and β-hydroxyethoxyethyl radicals.

By way of preferred compounds of formula (II'), the following may be mentioned:
4,5-dinitro-2-(β-hydroxyethoxy)phenol
4,5-dinitro-2-[β-(2-hydroxyethoxy)ethoxy]phenol
4,5-nitro-2-(β-methoxyethoxy)phenol.

The compounds of formula (I) can be used as direct dyes in dyeing compositions for dyeing keratinous fibres, and especially human hair.

The subject of the present invention is hence also a dyeing composition for keratinous fibres, and especially for human hair, containing at least one compound of formula (I) in a cosmetically acceptable medium.

The dyeing compositions according to the invention contain the compounds of formula (I) in proportions of between 0.001 and 5% by weight, and preferably between 0.01 and 3% by weight, relative to the total weight of the dyeing composition.

They can contain anionic, cationic, nonionic or amphoteric surfactants or mixtures thereof. These surfactant products are present in the compositions of the invention in proportions of between 0.5 and 55% by weight, and preferably between 4 and 40% by weight, relative to the total weight of the composition.

The cosmetic vehicle generally consists of water, but organic solvents can also be added to the compositions to solubilize compounds which would not be sufficiently soluble in water. Among these solvents, there may be mentioned lower alkanols such as ethanol and isopropanol, polyols such as glycerol, and glycols or glycol ethers such as 2-butoxyethanol, ethylene glycol, ethylene glycol monoethyl ether, propylene glycol, diethylene glycol monoethyl ether and monomethyl ether, as well as similar products and mixtures thereof. These solvents are preferably present in proportions ranging from 1 to 75% by weight, and especially from 5 to 50% by weight, relative to the total weight of the composition.

The compositions can preferably be thickened with compounds chosen from sodium alginate, gum arabic, xanthan gum, cellulose derivatives such as methylcellulose, hydroxyethylcellulose, hydroxypropylmethylcellulose and carboxymethylcellulose, and various polymers having the function of a thickener such as, more especially, acrylic acid derivatives. It is also possible to use inorganic thickening agents such as bentonite.

These thickening agents are preferably present in proportions of between 0.1 and 10% by weight, and especially between 0.5 and 3% by weight, relative to the total weight of the composition.

The compounds according to the invention can also contain various adjuvants customarily used in hair dyeing compositions, and especially penetrants, sequestering agents, film-forming agents, buffers and perfumes.

These compositions can take various forms such as liquid, cream or gel form, or any other form suitable for carrying out dyeing of hair. They can, in addition, be packed in aerosol cans in the presence of a propellant.

The pH of these dyeing compositions can be between 3 and 11.5, preferably between 5 and 11.5. This is adjusted to the desired value by means of an alcalinizing agent such as ammonia solution, sodium carbonate, potasssium carbonate or ammonium carbonate, sodium hydroxide or potassium hydroxide, alcanolamines such as mono-, di- or triethanolamine, or alkylamines such as ethylamine or triethylamine, or by means of an acidifying agent such as phosphoric, hydrochloric, tartaric, acetic, lactic or citric acid.

The dyeing compositions according to the invention can contain, in addition to the compounds according to the invention, other direct dyes such as azo dyes, for example 4-amino-2'-methyl-4'-[bis(hydroxyethyl)amino]azobenzene, or anthraquinone dyes such as, for example, 1,4,5,8-tetraaminoanthraquinone, and nitro dyes of the benzene series other than the compounds of formula (I), and more especially the following compounds:
3-nitro-4-amino-6-chloro-N-(β-aminoethyl)aniline
3-nitro-4-methylamino-N-(8-hydroxyethyl)aniline
3-nitro-4-amino-N-β-hydroxyethyl)aniline
[3-nitro-4-(β-hydroxyethyl)aminophenoxy]ethanol
3-nitro-4-(β-aminoethyl)amino-N-bis(β-hydroxyethyl)aniline
3-nitro-4-(β-hydroxyethyl)amino-6-chloroaniline
3-nitro-4-amino-6-methyl-N-(β-hydroxyethyl)aniline
N,N'-bis(β-hydroxyethyl)-4-nitro-ortho-phenylenediamine
2-nitro-N-(β-aminoethyl)aniline
2-methyl-6-nitroaniline
3-nitro-4-aminophenol
3-nitro04-(β-hydroxyethyl)aminophenol
3-nitro-4-amino-6-methylphenol
3-amino-4-nitrophenol
2-amino-3-nitrophenol
3-nitro-6-(β-hydroxyethyl)aminoanisole
3-(β,γ-dihydroxypropyl)amino-4-nitroanisole
3-methylamino-4-nitrophenoxy)ethanol
3-methylamino-4-nitrophenylβ,γ-dihydroxypropyl ether
N,N'-bis(β-hydroxyethyl)nitro-para-phenylenediamine
3-nitro-4-methylamino-N,N-bis(β-hydroxyethyl)aniline
3-nitro-4-(β-hydroxyethyl)amino-N,N-bis(β-hydroxyethyl)aniline
3-nitro4-(β-hydroxyethyl)aminoaniline
3-nitro-4-(γ-hydroxypropyl)amino-N,N-bis(β-hydroxyethyl)aniline.

The concentrations of these direct dyes, other than the dyes of formula (I), can be between 0.001 and 5% by weight relative to the total weight of the composition.

The present invention also relates to a process for dyeing keratinous fibres, and more especially human hair, by direct dyeing, which consists in applying on the fibres a composition as defined above, leaving the latter in place for 5 to 40 minutes, then rinsing the fibres, optionally washing them, rinsing them again and drying them.

The compositions according to the invention can also be employed in the form of hair setting lotions designed, at one and the same time, to endow the hair with a light colouring and to improve the shape-retention of the set. In this case, they take the form of aqueous, alcoholic or hydroalcoholic solutions containing at least one cosmetic resin, and they are applied on damp hair which has been washed and rinsed beforehand and which is optionally coiled and then dried.

The subject of the present invention is consequently a process for dyeing keratinous fibres, and especially human hair, which consists in applying a composition according to the invention containing at least one cosmetic resin on the washed and rinsed fibres, then in optionally coiling the fibres and in drying them.

The cosmetic resins used in the setting lotions can be, in particular, polyvinylpyrrolidone or crotonic acid-vinyl acetate, vinylpyrrolidone-vinyl acetate, maleic anhydride-butyl vinyl ether or maleic anhydridemethyl vinyc ether copolymers, as well as any other cationic, anionic, nonionic or amphoteric polymer customarily used in this type of composition. These cosmetic resins participate in the compositions according to the invention in the proportion of 0.5 to 3% by weight, and preferably 1 to 2% by weight, based on the total weight of the composition.

The present invention will be better illustrated by the following non-limitative examples:

EXAMPLE 1

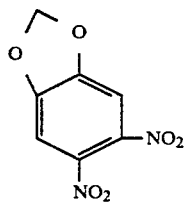

Preparation of the starting 4,5-methylenedioxy-1,2-dinitrobenzene according to D. S. Wulfman and C. F. Cooper, Synthesis, p. 924–925 (1978)

0.103 mol (17.2g) of 4,5-methylenedioxy-1-nitrobenzene is added in small portions in the course of 15 minutes to a mixture, cooled to −5° C., consisting of 125 ml of nitric acid (d=1.50) and 125 ml of nitric acid (d=1.40), the temperature being maintained at between 0° C. and 5° C. 1 hour after the addition is complete, the reaction mixture is poured onto 1 kg of ice; the expected product precipitates. After being dried hot in the presence of phosphorus pentoxide, it melts at 99° C. (literature 98° C. -100° C.). It can optionally be recrystallized from 96° strength ethanol.

Analysis of the product obtained gives the following results:

| Analysis | Calculated for $C_7H_4N_2O_6$ | Found |
|---|---|---|
| C % | 39.63 | 39.81 |
| H % | 1.90 | 1.93 |
| N % | 13.21 | 13.20 |
| O % | 45.26 | 45.15 |

EXAMPLE 2

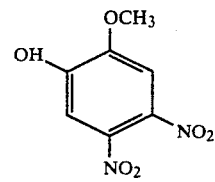

Preparation of 4,5-dinitro-2-methoxyphenol 0.1 mol (21.2 g) of 4,5-methylenedioxy-1,2-dinitrobenzene is added to a solution of 0.12 mol (16.8 ml) of triethylamine, 0.4 mol of sodium methylate (72 g of a 30% strength solution in methanol) and 60 ml of methanol. The mixture is heated for 10 minutes at the refluxing temperature of the methanol. After the mixture has been cooled to 0° C., the phenate of the expected product is drained. The phenate is dissolved in 300 ml of water at 60° C. The solution is filtered on paper in order to remove a resin. On cooling and neutralization of the filtrate with acetic acid, the expected product precipitates. After being dried, the 4,5-dinitro-2-methoxyphenol thereby obtained is recrystallized from isopropanol. It melts at 172° C. (literature: 177° C.).

Analysis of the product obtained gives the following results:

| Analysis | Calculated for $C_7H_6N_2O_6$ | Found |
|---|---|---|
| C % | 39.26 | 39.45 |
| H % | 2.82 | 2.75 |
| N % | 13.08 | 13.25 |
| O % | 44.83 | 45.02 |

EXAMPLE 3

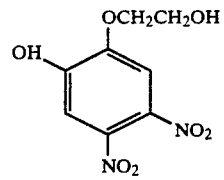

Preparation of 4,5-dinitro-2-(β-hydroxyethoxy)phenol 0.2 mol (13.2g) of potassium hydroxide pellets (85%) is added to 100 ml of ethylene glycol which has been heated beforehand to 50° C. 0.1 mol (21.2g) of 4,5-methylenedioxy-1,2-dinitrobenzene is added in a single portion to this solution. The heating is maintained for 2 hours.

The reaction medium is cooled. After dilution with water and neutralization with acetic acid, the expected product precipitates and is drained. After being dried, it is recrystallized from isopropanol. It melts at 196° C.

Analysis of the product obtained gives the following results:

| Analysis | Calculated for $C_8H_8N_2O_7$ | Found |
|---|---|---|
| C % | 39.35 | 39.30 |
| H % | 3.30 | 3.48 |
| N % | 11.47 | 11.22 |
| O % | 45.87 | 46.00 |

EXAMPLE 4

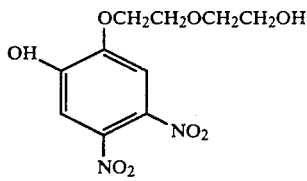

Preparation of 4,5-dinitro-2-[β-(2-hydroxyethoxy)ethoxy]phenol 0.4 mol (26.4g) of 85% pure potassium hydroxide pellets is added at 70° C. to 200 ml of diethylene glycol. 0.2 mol (42 4g) of 4,5-methylenedioxy-1,2-dinitrobenzene is added to this solution. The heating is maintained for 3½ hours. After dilution with ice-cold water and neutralization with 22 ml of acetic acid, the expected product precipitates. After being dried, it is recrystallized from 96° strength alcohol. It melts at 135° C. Analysis of the product gives the following results:

| Analysis | Calculated for $C_{10}H_{12}N_2O_3$ | Found |
|---|---|---|
| C % | 41.67 | 41.94 |
| H % | 4.20 | 4.25 |
| N % | 9.72 | 9.82 |
| O % | 44.41 | 44.12 |

EXAMPLE 5

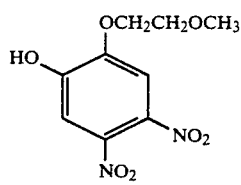

Preparation of 4,5-dinitro-2-(β-methoxyethoxy)phenol 0.2 mol (13.2 g) of potassium hydroxide pellets (85%) is added to 100 ml of ethylene glycol monomethyl ether which has been heated beforehand to 45° C. 0.1 mol (21.2 g) of 4,5-methylenedioxy-1,2-dinitrobenzene, prepared according to Example 1, is added to this solution in the course of 5 minutes. The heating is maintained for 1 hour.

The reaction medium is cooled. After dilution with water and neutralization with acetic acid, the expected product precipitates and is drained. After being dried, it is recrystallized from 96° strength ethyl alcohol. It melts at 98° C.

Analysis of the product obtained gives the following results:

| Analysis | Calculated for $C_9H_{10}N_2O_7$ | Found |
|---|---|---|
| C % | 41.86 | 41.76 |
| H % | 3.90 | 3.95 |
| N % | 10.85 | 10.90 |
| O % | 43.38 | 43.05 |

EXAMPLE 6

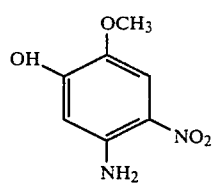

Preparation of 5-amino-2-methoxy-4-nitrophenol

A mixture consisting of 0.15 mol (32.1 g) of 4,5-dinitro-2-methoxyphenol, prepared in Example 2, 150 ml of formamide and 200 ml of 28% strength ammonia solution in water is heated to 95° C. for 8 hours in an autoclave. After the mixture is cooled, the expected product crystallizes. It is dissolved in the minimum quantity of dimethylformamide, and is then precipitated by adding water. It melts at 208° C.

Analysis of the product obtained gives the following results:

| Analysis | Calculated for $C_7H_8N_2O_4$ | Found |
|---|---|---|
| C % | 45.65 | 45.61 |
| H % | 4.38 | 4.45 |
| N % | 15.21 | 15.15 |
| O % | 34.75 | 34.67 |

EXAMPLE 7

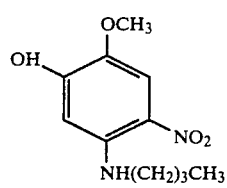

Preparation of 5-n-butylamino-2-methoxy-4-nitrophenol

A mixture consisting of 80 ml of n-butylamine, 10 ml of water and 0.1 mol (21.4 g) of 4,5-dinitro-2-methoxyphenol, prepared in Example 2, is heated under reflux. After 4 hours heating, the reaction medium is diluted with 800 g of ice-cold water; the expected product precipitates. After being drained and dried, it is taken up in 300 ml of dilute caustic soda and precipitated by adding acetic acid.

After recrystallization from a cyclohexane-ethyl acetate mixture, it melts at 94° C.

Analysis of the product obtained gives the following results:

| Analysis | Calculated for $C_{11}H_{16}N_2O_4$ | Found |
|---|---|---|
| C % | 54.99 | 55.13 |
| H % | 6.71 | 6.78 |
| N % | 11.66 | 11.48 |
| O % | 26.64 | 26.77 |

EXAMPLE 8

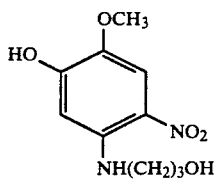

Preparation of
5-(γ-hydroxypropyl)amino-2-methoxy-4-nitrophenol

A mixture consisting of 0.2 mol (42.8 g) of 4,5-dinitro-2-methoxyphenol, prepared in Example 2, 0.6 mol (45.7 g) of 3-amino-1-propanol and 30 ml of water is heated at the refluxing temperature of water for 3 h 30 min.

The reaction medium is diluted with 150 ml of ice-cold water. After neutralization with acetic acid, the expected product crystallizes. After recrystallization from 96° strength alcohol, it melts at 149° C.

Analysis of the product obtained gives the following results:

| Analysis | Calculated for $C_{10}H_{14}N_2O_5$ | Found |
|---|---|---|
| C % | 49.58 | 49.41 |
| H % | 5.83 | 5.88 |
| N % | 11.57 | 11.50 |
| O % | 33.03 | 33.19 |

EXAMPLE 9

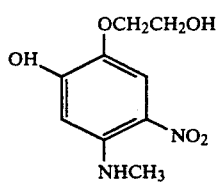

Preparation of
5-methylamino-2-(β-hydroxyethoxy)-4-nitrophenol

A mixture consisting of 0.115 mol (28.2 g) of 4,5-dinitro-2-(β-hydroxyethoxy)phenol, prepared in Example 3, in 300 ml of a 33% strength solution of methylamine in absolute ethanol and 100 ml of formamide is heated to 95° C. for 6 hours in an autoclave (pressure 5-6 kg/cm²). After the reaction medium has been cooled, the expected product crystallizes. It is recrystalized from formamide. It melts at 210° C.

Analysis of the product gives the following results:

| Analysis | Calculated for $C_9H_{12}N_2O_5$ | Found |
|---|---|---|
| C % | 47.37 | 46.02 |
| H % | 5.30 | 5.37 |
| N % | 12.28 | 13.78 |
| O % | 35.06 | 34.90 |

EXAMPLE 10

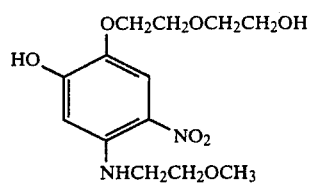

Preparation of
5-(β-methoxyethyL)amino-2-[β-(2-hydroxyethoxy)ethoxy]-4-nitrophenol A mixture prepared by adding 0.07 mol (20.2 g) of 4,5-dinitro-2-[β-(2-hydroxyethoxy)ethoxy]phenol, prepared according to Example 4, to 0.28 mol (21 g) of 2-methoxyethylamine and 15 ml of water is heated under reflux.

After 3 hours' heating, the reaction medium is diluted with 100 g of ice-cold water. On neutralization with acetic acid, the expected product precipitates. After recrystallization from ethyl acetate, it melts at 120° C.

Analysis of the product obtained gives the following results:

| Analysis | Calculated for $C_{13}H_{20}N_2O_7$ | Found |
|---|---|---|
| C % | 49.36 | 49.43 |
| H % | 6.37 | 6.43 |
| N % | 8.86 | 8.77 |
| O % | 35.41 | 35.15 |

DYEING EXAMPLE 1

The following dyeing mixture is prepared:
5-Amino-2-methoxy-4-nitrophenol: 0.25 g
2-Butoxyethanol: 10.0 g
96° strength alcohol: 10 0 g
CELLOSIZE W.P. 03: 2.0 g
Cetyldimethylhydroxyethylammonium chloride: 2.0 g
2-Amino-2-methyl-1-propanol in 25% solution in water: 1.0 g
Water q.s.: 100 g
pH 9.4

When applied for 20 minutes at 28° C. on hair which is naturally 90% white, this mixture endows it, after shampooing and rinsing, with a lustrous green-yellow colouring.

DYEING EXAMPLE 2

The following dyeing mixture is prepared:
5-n-Butylamino-2-methoxy-4-nitrophenol: 0.4 g
Propylene glycol: 10.0 g
96° strength alcohol: 10.0 g
CARBOPOL 934: 2.0 g
Monoethanolamine in 20% solution in water: 1.0 g
Water q.s.: 100 g pH 4.5

When applied for 25 minutes at 30° C. on hair which is naturally 90% white, this mixture endows it, after shampooing and rinsing, with a powerful orange-yellow colouring.

DYEING EXAMPLE 3

The following dyeing mixture is prepared:
5 5-Methylamino-2-(β-hydroxyethoxy)-4nitrophenol: 0.1 g
2-Butoxyethanol: 10.0 g
CELLOSIZE W.P. 03: 2.0 g
Ammonium lauryl sulphatae: 5.0 g
4% Ammonia solution: 1.0 g
Water q.s.: 100 g
pH 8.7

When applied for 40 minutes at 28° C. on bleached hair, this mixture endows it, after shampooing and rinsing, with a mimosa yellow colouring.

DYEING EXAMPLE 4

The following dyeing mixture is prepared:
5-(γ-Hydroxypropyl)amino-2-methoxy-4nitrophenol: 0.6 g
2-Butoxyethanol: 20.0 g
COMPERLAN KD: 2.2 g
Lauric acid: 0.8 g
Ethylene glycol monoethyl ether: 2.0 g
Monoethanolamine: 1.0 g
Water q.s.: 100 g
pH 6.5

When applied for 15 minutes at 30° C. on bleached hair, this mixture endows it, after shampooing and rinsing, with a powerful golden yellow colouring.

DYEING EXAMPLE 5

The following dyeing mixture is prepared:
5-(β-Methoxyethyl)amino-2-[β-(2-hydroxyethoxy)ethoxy]-4-nitrophenol: 1.0 g
96° strength alcohol: 5.0 g
2-Butoxyethanol: 5.0 g
TWEEN 80: 12.0 g
Oleic acid: 20.0 g
2-amino-2-methyl-1-propanol in 25% solution in water: 1.0 g
Water q.s.: 100 g
pH 6.2

When applied for 25 minutes at 30° C. on hair which is naturally 90% white, this mixture endows it, after shampooing and rinsing, with a buttercup yellow colouring.

The various trade names used in the examples above are clarified in further detail below:

CARBOPOL 934: Crosslinked acrylic acid polymer :of MW 2 to 3 million sold by Goodrich Chemical Company TWEEN 80: Polyoxyethylenated sorbitol monooleate COMPERLAN KD: Coconut fatty acid diethanolamide, sold by HENKEL CELLOSIZE WP 03: Hydroxyethylcellulose, sold by UNION CARBIDE

What is claimed is:

1. A process for preparing a 3-amino-4-nitrophenol having the formula

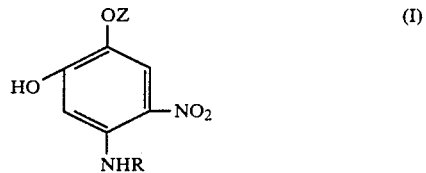

wherein
Z represents —$CH_2$—W wherein W represents hydrogen, alkyl having 1-6 carbon atoms, hydroxyalkyl wherein the alkyl moiety has 1-6 carbon atoms, polyhydroxyalkyl wherein the alkyl moiety has 2-6 carbon atoms, alkoxyalkyl wherein the alkoxy moiety has 1-3 carbon atoms and the alkyl moiety has 1-6 carbon atoms or hydroxyalkoxyalkyl wherein the alkoxy moiety has 1-3 carbon atoms and the alkyl moiety has 1-6 carbon atoms and
R represents hydrogen, alkyl having 1-6 carbon atoms, hydroxyalkyl having 1-6 carbon atoms, polyhydroxyalkyl having 2-6 carbon atoms or alkoxyalkyl wherein the alkoxy moiety has 1-3 carbon atoms and the alkyl moiety has 1-6 carbon atoms, said process comprising (i) in a first step, reacting an alcohol of the formula ZOH, wherein Z has the meaning given above, in the presence of a strong base, with 1,2-dinitro-4,5-methylenedioxybenzene at a temperature ranging from 20° to 200° C. under ambient pressure so as to produce a compound of formula II in accordance with the following reaction scheme:

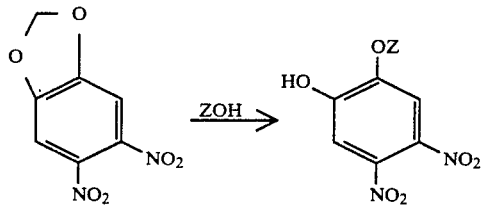

wherein Z has the meaning given above, and (ii) in a second stage, selectively substituting the $NO_2$ group in position para to the OZ group by a NHR group using ammonia or an amine of the formula $RNH_2$ wherein R has the meaning given above, at the refluxing temperature of the reaction medium.

2. The process of claim 1 wherein the strong base employed in the first stage is potassium hydroxide or a sodium or potassium alcoholate derived from said ZOH alcohol.

3. The process of claim 2 wherein said ZOH alcohol or said alcoholate is used in excess and said excess serves as a solvent.

4. The process of claim 1 carried out at the refluxing temperature of said ZOH alcohol.

5. The process of claim 1 wherein said second stage is carried out in the presence of a polar solvent.

6. The process of claim 5 wherein said polar solvent is water, a $C_1$-$C_4$ lower alcohol or amide.

7. The process of claim 1 wherein said second stage is carried out under pressure.

* * * * *